United States Patent [19]

Jablonski

[11] Patent Number: 5,674,469
[45] Date of Patent: Oct. 7, 1997

[54] GAS-EXCHANGE METHOD OF MAKING GAS-FILLED MICROSPHERES

[75] Inventor: Edward G. Jablonski, Escondido, Calif.

[73] Assignee: Molecular Biosystems, Inc., San Diego, Calif.

[21] Appl. No.: 484,338

[22] Filed: Jun. 7, 1995

[51] Int. Cl.$^6$ .............................. A61K 49/04; A61B 8/14
[52] U.S. Cl. ................................... 424/9.52; 128/662.02
[58] Field of Search ........................ 424/9.52, 9.5, 424/9.51, 450, 489; 128/662.02; 264/4.1

[56] References Cited

U.S. PATENT DOCUMENTS

| | | |
|---|---|---|
| 4,572,203 | 2/1986 | Feinstein . |
| 4,718,433 | 1/1988 | Feinstein . |
| 5,149,543 | 9/1992 | Cohen et al. . |
| 5,393,524 | 2/1995 | Quay . |
| 5,409,688 | 4/1995 | Quay . |
| 5,413,774 | 5/1995 | Schneider et al. . |

FOREIGN PATENT DOCUMENTS

| | | |
|---|---|---|
| 0 324 938 | 7/1989 | European Pat. Off. . |
| 0 554 213 | 8/1993 | European Pat. Off. . |
| 2280389 | 2/1995 | United Kingdom . |
| WO93/05819 | 4/1993 | WIPO . |
| WO94/16739 | 8/1994 | WIPO . |
| WO95/01187 | 1/1995 | WIPO . |
| WO95/06518 | 3/1995 | WIPO . |

OTHER PUBLICATIONS

Ophir et al., "Contrast Agents in Diagnostics Ultrasound," *Ultrasound in Med. & Biol.* 15(4):319–333 (1989).

Porter et al., "Visually Discernible Myocardial Echocardiographic Contrast After Intravenous Injection of Sonicated Dextrose Albumin Microbubbles Containing High Molecular Weight, Less Soluble Gases," *J. of the American College of Cardiology* 25(2):509–515 (1995).

March, *Advanced Organic Chemistry*, 4th Edition, pp. 417–418, John Wiley & Sons, New York, New York (1992).

*Primary Examiner*—Gary E. Holliden
*Assistant Examiner*—Michael G. Hartley
*Attorney, Agent, or Firm*—Morrison & Foerster LLP

[57] ABSTRACT

Ultrasonic imaging agents comprising an insoluble gas may be made by a new process of gas exchange. A solution is supersaturated with the insoluble gas and then contacted with a conventional air-filled microsphere suspension in order to effectuate a gas exchange process. The insoluble gas-containing microsphere exhibits increased pressure resistance and stability over microspheres in which the gas exchange was performed passively.

8 Claims, No Drawings

GAS-EXCHANGE METHOD OF MAKING GAS-FILLED MICROSPHERES

TECHNICAL FIELD

This invention is in the field of ultrasound contrast agents. More particularly, it concerns a method of making pressure resistant microspheres by exposing them to super saturated solutions of insoluble gas.

BACKGROUND

Gas-filled microsphere ultrasound agents are well-known in the art. For example, Ophir and Parker (Ultrasound in Medicine and Biology 15(4):319–333 (1989)) describe several types of gaseous ultrasound contrast agents. The two principal types are gas bubbles suspended in a liquid (sometimes referred to as liquid-gas emulsions or foams, but hereinafter referred to as "microbubble suspensions") and encapsulated gases (commonly called "microspheres"). The present invention concerns a novel method for making microspheres. Initially, microspheres were made by sonication. U.S. Pat. No. 4,572,203 describes the preparation of microspheres by subjecting biocompatible liquids to ultrasonic energy. U.S. Pat. No. 4,718,433 teaches the sonication of solutions of heat-denaturable proteins, such as human serum albumin, to produce more persistent microspheres.

Other contrast agents include microspheres which entrap gases other than air. EP 0 554,213 teaches a method of making water insoluble gas-filled microspheres. The microspheres are first produced by "any suitable conventional technique" and the internalized gas is replaced with a more suitable gas by passive exchange. This is accomplished by bubbling, or sweeping the surface of a suspension with gas.

Alternatively, a suspension of microspheres can be incubated under a headspace of the desired gas in a buffer for an adequate amount of time. The gas headspace in the vessel may be replenished if necessary. The inability to exchange relatively water insoluble gases into air-filled albumin microspheres by passive diffusion of headspace gas into a suspension has been demonstrated experimentally. When this method is performed using ALBUNEX® air-filled albumin microspheres (Molecular Biosystems, Inc., San Diego, Calif., a very small number of albumin microspheres having improved pressure resistance can be produced by passive gas exchange. The survivability of the material is very low with most of the loss of the entrained gas occurring in the first hour of exposure to one of the insoluble gases. The air core of air-filled albumin microspheres diffuses out faster than the insoluble gas can dissolve into a surrounding solution, effectively destroying the bulk of the microspheres. The extent of the destruction is a function of the solubility of the gas which is to be exchanged. Therefore, the resulting composition is a very weak ultrasound formulation, making this procedure a minimal success.

Porter, T. R., and Xie, F. (JACC 25:2 (1995) pp. 509–515) teach a method of preparing $SF_6$ albumin/dextrose microspheres by incubating air-filled material with $SF_6$ gas in a syringe for 60 minutes under rocking agitation. The product must be immediately injected once it is decanted from the syringe. These preparations require a concentration of a factor of 8 in order to demonstrate some in vivo efficacy. It is hypothesized that this is due to the loss of the gas from the microspheres. Concentrated product is further boosted by inhalation of the core gas by the patient during imaging. This results in visually discernable myocardial contrast, but still fails to yield visualization of the inferior and posterior walls. Mean contrast time is in mere seconds. Non-concentrated product gives no visible and minimal quantifiable contrast in the anterior myocardium.

Lambert et al. (WO 95/01187) describe a method of making microspheres that utilizes mechanical cavitation. This method was considered an improvement over the previous methods of making microspheres containing insoluble gases because the microspheres were formed absent the presence of air, thereby resulting in microspheres substantially filled with only the insoluble gas. The microspheres filled entirely with the insoluble gases display increased pressure resistance and stability. However, the requirement of mechanical cavitation is somewhat costly. Therefore, there still exists a need for a simple method of making insoluble gas-filled microspheres which produces a more stable product.

DISCLOSURE OF THE INVENTION

The present invention relates to a method for making microspheres which does not require the use of mechanical cavitation. This method is nondestructive and results in microspheres which are substantially filled with a water insoluble gas and which display increased pressure resistance.

One aspect of the invention is a method for making pressure resistant, gas-filled microspheres for use as an ultrasonic imaging agent which comprises the steps of:

(a) exposing a solution to a high pressure water insoluble gas; and (b) using the resultant solution as a bath for air-filled microspheres thereby resulting in the exchange of the insoluble gas for the air.

A further aspect of the invention is a method for enhancing the contrast of tissues and/or organs of a patient in an ultrasound image thereof comprising:

(a) injecting the above-described composition into the patient;

(b) applying ultrasonic energy to said tissue and/or organ;

(c) detecting ultrasonic energy that is reflected from the tissues and/or organs; and (d) translating the reflected energy into an image.

MODES FOR CARRYING OUT THE INVENTION

As used herein the terms "water insoluble" and "insoluble" are used interchangeably and intend a gas having a solubility in water at 25° C., atmospheric pressure less than 0.01 mL/min. Preferably, the diffusivity of the insoluble gas is less than $4 \times 10^{-5}$ cm$^2$/sec in water at 25° C.

The term "supersaturated" intends a liquid solution containing dissolved water insoluble gas at a concentration grater than the concentration of said gas in said solution at one atmosphere of pressure.

It is now possible to nondestructively create insoluble gas-filled microspheres from air-filled albumin microspheres by increasing the rate of exchange of the external gas into the microsphere. This may be accomplished by increasing the concentration of the insoluble gas in the liquid in which the air-filled microspheres are suspended. The concentration of a dissolved gas in solution is a function of the pressure above the solution. The concentration of any gas in solution may be increased by increasing the pressure on the solution. Unfortunately, air from inside of air-filled microspheres will also dissolve more readily as well, as witnessed by destruction of air-filled microspheres under the application of a sufficient pressure. In order to create sufficient gas exchange between air and a less soluble gas, the less soluble gas concentration must be elevated without exposing air-filled microspheres to a pressurization. This can be accomplished by exposing a solution, which is passing through gas permeable tubing, to high pressure insoluble gas. The solution will become charged with the insoluble gas as a function of the pressure, and is then used to bathe a suspension of air-filled microspheres which readily undergo gas exchange.

The insoluble gas for exchange need only be biocompatible. Such gases are well-known in the art and include, but are not limited to the hydrocarbon, halogenated hydrocarbon, or perfluorocarbon series or mixtures thereof. Preferred gases include perfluoromethane, perfluoroethane, perfluoropropane, perfluorobutane, sulfur hexafluoride or other fluorinated compounds which are either linear, branched or cyclic. A small percentage of air may be present to prevent the microspheres from completely collapsing during the exchange.

The air-filled microsphere typically has a shell material which is an amphiphilic biocompatible material. Amphiphilic materials have both hydrophilic and hydrophobic groups. Different classes of materials that are generally used for forming microsphere shells include, but are not limited to lipids, proteins (both naturally occurring and synthetic amino acid polymers), synthetic organic polymers, and mixtures or copolymers thereof.

Lipid shells may be formed from either naturally occurring or synthetic lipids, for example, phospholipids, such as phosphoglycerides, phosphatidic acid, phosphatidylcholine, phosphatidyl serine, phosphatidylethanolamine, phosphatidyl inositol, phosphatidyl glycerol, diphosphatidyl-glycerol (cardiolipin); glycolipids, such as cerebrosides, galactocerebrosides, gluco-cerebrosides, sphingomyelin, sphingolipids, derivatized with mono-, di-, and trihexosides, sulfatides, glycosphingolipid, and lysophosphatidylcholine; unsaturated fatty acids, such as palmitoleic acid, oleic acid, vaccenic acid, linoleic acid, α-linolenic acid, and arachadonic acid; saturated fatty acids, such as myristic acid, palmitic acid, stearic acid, arachidic acid, behenic acid, lignoceric acid, and cerotic acid; mono-, di-, and triglycerides; and steroids, such as cholesterol, cholesterol esters, cholestanol, ergosterol, coprostanol, squalene, and lanosterol.

Lipid shells may also optionally incorporate proteins, amino acid polymers, carbohydrates or other substances useful for altering the rigidity, elasticity, biodegradability, and/or biodistribution characteristics of the shell. Incorporation of sterols is particularly useful in increasing the rigidity of the shell. The rigidity of the shell can also be enhanced by cross-linking, for example, by irradiation.

Protein shell material includes both naturally occurring filmogenic proteins and synthetic amino acid polymers which herein are both generally referred to as being in the class of shell materials described as "proteins." The term "filmogenic" intends a soluble protein that is able to form a shell or film about a biocompatible liquid core when the protein is insolubilized by cavitation. Suitable proteins include naturally occurring proteins such as albumin, gamma-globulin (human), apo-transferrin (human), β-lactoglobulin, urease and lysozyme, as well as synthetic amino acid polymers. Particularly well-suited for the present invention is albumin, and more particularly, human albumin.

Synthetic organic polymers are also suitable for forming the microsphere shells. These polymers can consist of a single repeating unit or different repeating units which form a random, alternating or block-type copolymer. See, for instance, PCT application WO95/06518, the disclosure of which is incorporated herein by reference. These organic polymers include cross-linked polyelectrolytes such as phosphazenes, imino-substituted polyphosphazenes, polyacrylic acids, polymethacrylic acids, polyvinyl acetates, polyvinyl amines, polyvinyl pyridine, polyvinyl imidazole, and ionic salts thereof. Cross-linking of these polyelectrolytes is accomplished by reaction of multivalent ions of the opposite charge. Further stabilization can be accomplished by adding a polymer of the same charge as the polyelectrolyte. See U.S. Pat. No. 5,149,543 which is incorporated herein by reference.

Additional synthetic organic monomeric repeating units which can be used to form polymers suitable for shell materials within the present invention are hydroxyacids, lactones, lactides, glycolides, acryl containing compounds, aminotriazol, orthoesters, anhydrides, ester imides, imides, acetals, urethanes, vinyl alcohols, enolketones, and organosiloxanes.

Shell forming materials suitable for the present invention, or the resulting microspheres, may be chemically modified for the purpose of organ/tissue targeting or quenching immunogenic activity (i.e., modification with antibodies or polyethylene glycol). The materials may also be modified by incorporation of fluorine-containing moieties. The inclusion of such moieties in the shell may make the shell less permeable to water and may enhance interaction between the shell and a fluorine-containing liquid core. The shell may be so modified by reacting the material with a reactive fluorine-containing compound to form a covalently bound complex.

Preferred reactive compounds for modifying proteins are either alkyl esters or acyl halides which are capable of reacting with the protein's amino groups to form an amide linkage via an acylation reaction (see ADVANCED ORGANIC CHEMISTRY pp. 417–418 (John Wiley & Sons, New York, N.Y., 4th ed., 1992)). The reactive compound is preferably added to the vaporized liquid compound before the vapor is mixed with the protein solution prior to microsphere formation. For example, the reactive compound can be added to the vapor phase by bubbling the vapor through a solution of the reactive compound. This solution is kept at a constant temperature which is sufficient to introduce a desired amount of reactive compound into the vapor phase. The resultant mixture, which now contains the liquid vapor and the reactive compound, is then charged to the cavitation process.

Suitable fluorine-containing alkyl esters and acyl halides are diethyl hexafluoroglutarate, diethyl tetrafluorosuccinate, ethyl heptafluorobutyrate, ethyl pentafluoropropionate, ethyl perfluorooctanoate, nonafluoropentanoyl chloride, perfluoropropionyl chloride, hexafluoroglutaryl chloride, and heptafluorobutyryl chloride.

In addition to the use of acyl halides and acid esters described above, it is well known to those skilled in synthetic organic chemistry that many other fluorine-containing reactive compounds can be synthesized, such as aldehydes, isocyanates, isothiocyanates, epoxides, sulfonyl halides, anhydrides, acid halides, and alkyl sulfonates, which contain perfluorocarbon moieties ($-CF_3$, $-C_2F_6$, $-C_3F_8$, $-C(CF_3)_3$). These reactive compounds can then be used to introduce fluorine moieties into any of the shell materials by choosing a combination which is appropriate to achieve covalent attachment of the fluorine moiety.

Sufficient fluorine should be introduced to decrease the permeability of the microparticle shell to the aqueous environment. The shell material will preferably contain 0.5 to 20 percent by weight, and more preferably 1 to 10 percent by weight fluorine.

The method of making the insoluble gas-filled microspheres can be effectuated by any method whereby a liquid is supersaturated with the gas of choice for exchange with the air in the microsphere, and then brought in contact with the suspension of air-filled microspheres, creating gas exchange and resulting in the transfer of the insoluble gas into the microsphere.

This can be performed, i.e., by bringing a buffered, aqueous solution which is compatible with the shell stability of the microsphere (e.g., normal saline solution) into contact with the insoluble gas of choice which has been subjected to an increase in pressure sufficient to result in the solution becoming supersaturated. The amount of pressure which is needed will vary depending upon the gas that is chosen for the exchange, being limited by the condensation point of the gas. The insoluble gas pressure will generally be 2–5 atm above ambient pressure.

After the solution has been supersaturated with the insoluble gas, it may be brought into contact with the air-filled microsphere suspension and allowed to react over time sufficient to effect gas exchange. The time needed will vary depending upon the gas solubility, supersaturated concentration, and efficiency of exposing the air-filled microspheres to the gas solution. The time needed for exchange can be determined by monitoring the air-filled microsphere suspension with an oxygen probe.

Typically, the percent of gas that will be exchanged is within the range of 50–80%. Population concentration may be expected to decrease in the range of 0–10%. Mean diameter of the microspheres can be expected to decrease within the range of 20–30%.

The resulting pressure resistant microsphere suspensions of the invention are useful as an ultrasound contrast agent to enhance the ultrasound image of body tissues or organs such as the heart, kidney and brain. They are particularly useful for imaging the chamber, septum and posterior/lateral wall of the heart. Furthermore, the increased persistence of the agent makes it useful for target-specific applications, as they generally require a longer period of time for the agent to either reach the target and/or accumulate in a sufficient quantity to yield good images.

The microspheres are used in the form of a suspension in a sterile, aqueous, injectable vehicle. Such vehicles are well-known in the art. The concentration of microspheres in the suspension will normally be in the range of $1 \times 10^7$ to $1 \times 10^{10}$, more usually $1 \times 10^8$ to $1 \times 10^9$ per ml of suspending medium. The mean diameter is in the range of 1–10 microns, typically 3–4 microns. Saline is a preferred vehicle.

The invention is further illustrated by the following examples. These examples are not intended to limit the invention in any manner.

EXAMPLE 1—Prior Art Method of Passive Gas Exchange

The gas exchange method was carried out according to the preferred embodiment of EPA 0 554 213. The operation was performed under conditions designed to maintain sterility of the microsphere suspensions. Specifically, the vials were handled by gloved technicians in a CEPA filtered hood, periodically cleaned with 70% IPA. All needles and syringes were individually packaged and guaranteed sterile by the manufacturer. Insoluble gas reagents were filtered through a 0.22 micron in-line filter. Microscopic examination of sample vials revealed no bacterial growth for the duration of this investigation.

Vials of ALBUNEX® (Molecular Biosystems, Inc., San Diego, Calif.) contrast agent were placed on a hematology mixer at room temperature for several minutes. The ALBUNEX® suspension was observed to become uniform and homogeneous. The plastic cap was removed and a 25G1½ needle was fixed to a 5 cc syringe and inserted through the septum into the ALBUNEX®. Four cc of ALBUNEX® was slowly withdrawn. The syringe was removed, leaving the needle in place in the ALBUNEX®. A gas line with positive flow of 10 cc/min. was fixed to this needle. The gas bubbled up through the ALBUNEX® and the emerging coarse foam rose in the vial and emerged through the vent needle, effectively displacing the air. The gas was allowed to percolate for several seconds to ensure maximum gas content in the head space. The gas line needle was removed from the septum, followed by the vent needle. No immediate change in the suspension was observed. There was no indication of residual positive pressure in the vials upon opening either at one hour or at 4 days later. Control vials with an air head space were prepared by simply removing 4 cc of ALBUNEX® as described above, and then removing the vent and syringe needles from the septum. All the vials were stored upright, at rest, and at room temperature for up to 7 days.

Assays: Control vials with an air headspace and vials with $SF_6$, perfluoroethane (PFE), perfluoropropane (PFP), and perfluorobutane (PFB) head space were analyzed in duplicate. The vials were placed on a hematology mixer to render the suspension homogeneous. The cap and rubber septum were removed and the aliquots were taken for pressure resistance measurements, population dynamics analysis, photomicroscopy, and echogenicity.

Photomicroscopy was accomplished at 400× using an Olympus C-35AD-$ SLR camera coupled to an Olympus BH-2 microscope using 100 ASA film at an exposure of 4 seconds.

Population dynamics was assessed with a Coulter Multisizer II using a 50 micron aperture. Parameters of particle concentration, mean size, size distribution and entrapped gas volume were recorded.

Pressure resistance measurements were accomplished by a method similar to that reported in the reference. A sample of microspheres was diluted in aerated PBS to approximately 1 OD at 600 nm in a 3 ml necked cuvette. The neck was attached to a nitrogen pressure source and the cuvette placed in the spectrophotometer. The pressure in the cuvette was increased linearly to 5 psi over 150 seconds, at which time the pressure was rapidly released. The optical density at 600 nm was recorded. The linear pressure ramp was produced by a computer controlled valve and a pressure transducer. Echogenicity measurements were performed on samples after 7 days incubation at room temperature using an in vitro agar phantom with a 400 ml closed loop, circulating at 200 ml Isoton/min. The output from the HP SONUS ultrasound machine was recorded on videotape. All determinations were performed with a 5MHz transducer.

Results:

1. Microscopy.

a. Appearance of air head space is unchanged from ALBUNEX® at all time points.

b. $SF_6$ exchanged microspheres were badly depleted after the first hour.

c. Perfluoroethane exchanged microspheres greater than 5 microns disappeared entirely after the first hour.

c. Perfluoropropane exchanged microspheres were reduced to debris after the first hour.

d. Perfluorobutane exchanged microspheres were hard to locate after the first hour.

2. Coulter counts.

Control vials of microspheres with an air head space were indistinguishable from ALBUNEX® by all counting parameters and remained relatively unchanged for the duration of the experiment. Vials containing the insoluble gas in the head space exhibited a loss of encapsulated gas as a function of gas solubility. Vials filled with $SF_6$, PFE, PFP, and PFB decreased 82%, 95%, 99%, and 99.8%, respectively, in microsphere gas content within the first hour. Mean microsphere size was also reduced as a function of gas solubility. Total particle concentration was maintained for $SF_6$ in the first hour, but decreased for the other gases to as low as 2% for the PFB exchanged microspheres. Total particle concentration was not as drastically affected as total gas content because the shell debris is also counted.

3. Pressure Resistance.

The relatively small number of surviving microspheres exhibited increased pressure stability as a function of gas solubility. In the case of the PFP and PFB samples, however, there were almost no microspheres left to exhibit pressure resistance after 4 days.

4. Echogenicity.

ALBUNEX® is strongly echogenic at a dilution of $2.5 \times 10^{-5}$, and the image persists for greater than 1 minute in the circulating loop. The echogenicity at this dilution was unchanged after 7 days.

a. $SF_6$ exchanged microspheres exhibited strong and persistent echo at $2.5 \times 10^{-4}$ dilution (10× control), but were not echogenic at $2.5 \times 10^{-5}$ dilution.

b. PFE exchanged microspheres had a faint echo at $2 \times 10^{-3}$ dilution (100× control). The image persisted for only a few seconds.

c. PFP and PFB could not produce an echo at the minimum dilution of $2 \times 10^{-3}$.

EXAMPLE 2—Method of Pressurized Gas Exchange

Apparatus: An artificial lung was created by winding 100 feet of one eighth inch gas permeable tubing around an appropriate cylindrical support (chicken wire cage). This structure was inserted into a pressurizable container equipped with an inlet and outlet port. The ends of the tubing were plumbed to the ports on the inside of the container. This allowed liquid to pass into the container and exit while being entirely confined to the tubing. The container was also equipped with a gas inlet port and a pressure gauge. Normal saline was pumped through the lung at 100 ml/minute under 3 atmospheres pressure of perfluoroethane. Air concentration of the effluent was monitored by an in-line oxygen sensor, and determined to be less than 4% of saturation. The perfluoroethane supersaturated saline was directed into the bottom of a stirred 2 liter glass tank containing dialysis bags filled with ALBUNEX® suspension. The tank was allowed to drain from a top port. A second oxygen probe monitored a steady drop in dissolved air in the tank over 5 hours. When the dissolved air concentration decreased to 12% of saturation, the contents of the bags were transferred to sealed glass vials.

Results: Population dynamics: Starting ALBUNEX® material exhibited a concentration of $5.1 \times 10^8$ particles/ml, encapsulated volume of 0.068 ml/ml, and a mean diameter of 4.25 μ. Perfluoroethane treated ALBUNEX® decreased 5% in volume and the mean size was reduced to 3.1 μ. The concentration remained relatively unchanged.

Pressure resistance: Pressure resistance was assessed by monitoring the increase in light transmission through a suspension of microspheres having an initial optical density of one under an applied pressure of 3.5 psi. The ALBUNEX® sample clarified and was completely destroyed by the application of 3.5 psi. The perfluoropentane-exchanged material was 25% resistant.

EXAMPLE 3—Alternate Method of Pressurized Gas Exchange

Insoluble gas-exchanged microspheres may also be produced by contacting air-filled microspheres with the supersaturated solution as it is produced flowing through the lung. This on-line method would require a suspension of air-filled microspheres to be pumped through the lung in a gas permeable tubing and exposing the microspheres to insoluble gas as it is forced to dissolve in the carrying liquid. Pressure effects on the microsphere are reduced by the use of slow flow rates and larger diameter gas permeable tubing.

Modifications of the above-described modes for carrying out the invention that are obvious to those of skill in the art are intended to be within the scope of the following claims.

I claim:

1. A method of making an ultrasound contrast agent comprising an insoluble biocompatible gas encapsulated by a biocompatible amphiphilic shell material, said method comprising:

(a) providing a suspension of microspheres of air encapsulated by said shell material;

(b) preparing a solution which is supersaturated with an insoluble biocompatible gas; and (c) contacting the solution of (b) with the suspension of (a) for a sufficient amount of time to permit the air in the microsphere to exchange with the insoluble gas, whereby the microspheres are maintained at ambient pressure.

2. The method of claim 1 wherein the shell material is a heat-insolubilized filmogenic protein.

3. The method of claim 1 wherein the shell material is human serum albumin.

4. The method of claim 1 wherein the insoluble gas is selected from the group consisting of hydrocarbons, halogenated hydrocarbons, perfluorocarbons, or mixtures thereof.

5. The method of claim 4 wherein the insoluble gas is perfluoroethane.

6. The method of claim 4 wherein the insoluble gas is perfluoropropane.

7. The method of claim 4 wherein the insoluble gas is perfluorobutane.

8. The method of claim 4 wherein the insoluble gas is $SF_6$.

* * * * *